United States Patent
Finkelman et al.

(10) Patent No.: US 6,824,986 B1
(45) Date of Patent: Nov. 30, 2004

(54) METHODS FOR MEASURING IN VIVO CYTOKINE PRODUCTION

(75) Inventors: Fred D. Finkelman, Cincinnati, OH (US); Suzanne C. Morris, Mason, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/167,088

(22) Filed: Oct. 6, 1998

Related U.S. Application Data

(60) Provisional application No. 60/061,167, filed on Oct. 6, 1997.

(51) Int. Cl.$^7$ ............................................... G01N 33/53
(52) U.S. Cl. ....................... 435/7.1; 435/7.5; 435/7.23; 435/7.24; 435/7.92; 435/375; 435/287.2; 436/506; 436/507; 436/512; 436/513; 436/548; 436/177
(58) Field of Search .......................... 435/7.1, 7.5, 7.23, 435/7.25, 7.71, 7.72, 7.8, 7.92, 69.3, 69.4, 69.5, 69.6, 69.7, 287.2, 375; 436/501, 506, 507, 512, 513, 518, 519, 523, 527, 529, 534, 548, 800, 808, 540, 546, 177

(56) References Cited

U.S. PATENT DOCUMENTS

| | | | | |
|---|---|---|---|---|
| 4,271,140 A | * | 6/1981 | Bunting | 424/1 |
| 4,486,530 A | | 12/1984 | David et al. | 435/7 |
| 5,587,294 A | | 12/1996 | Tamarkin et al. | 435/7.93 |
| 5,612,034 A | | 3/1997 | Pouletty et al. | 424/184.1 |
| 6,022,541 A | * | 2/2000 | Senger et al. | 424/172.1 |

OTHER PUBLICATIONS

Ruedl et al., A novel and sensitive method for the detection of secreted cell products using time-resolved fluorescence, Journal of Immunological Methods 168 : 61–67 (1994), Sep. 7, 1993.*

Mukaida et al., Establishment of a highly sensitive enzyme–linked immunosorbent assay for the interleukin–1a employing a fluorogenic substrate, Journal of Immunological Methods, 107 : 41–46 (1998) Sep. 21, 1987.*

Morris et al., Effects of IL–12 on in vivo cytokine gene expression and immunoglobulin isotype selection, Journal of Immunological Methods, 152 : 1047–1056 (1994) Jul. 29, 1993.*

Gosling J., A Decade of Development in Immunoassay Methodology, Clin. Chem. 36 (8): 1408–1427 (1990).*

J. Immunol; 151:1235 (1993).

* cited by examiner

Primary Examiner—Christopher L. Chin
Assistant Examiner—Gailene R. Gabel
(74) Attorney, Agent, or Firm—Frost Brown Todd LLC

(57) ABSTRACT

The present invention involves techniques for evaluating in vivo cytokine production through the in vivo capture of secreting cytokines by labeled cytokine-binding reagents, followed by in vitro measurement of serum levels of captured cytokine. The methods of the present invention make use of the ability of a neutralizing antibody to a cytokine, when injected into a person or expierimental animal, to bind that cytokine and prevent its catabolism, excretion, or binding to a cytokine receptor. This causes the cytokine, which may normally have a very short in vivo half life, to accumulate in vivo as a cytokine/anti-cytokine antibody complex. If the anti-cytokine antibody is either labeled with a molecule that can be bound by another molecule (e.g.; biotin, which is bound by avidin or streptavidin), or is itself capable of being bound by another molecule (e.g.; a rat anti-cytokine antibody could be bound by an anti-rat immunoglobulin antibody), and the cytokine can also be bound by an antibody that recognizes a site distinct on the cytokine molecule from the site bound by the injected, neutralizing antibody, than the concentration of the cytokine/anti-cytokine complex in serum or other biological fluid can easily be assayed by a modified ELISA. This assay may be used with target analytes other than cytokines, which may include hormones, drugs or other analytes in a human or aninial. The target analyte is preferably a macromolecule, more preferably a protein, and most preferably a cytokine.

30 Claims, No Drawings

METHODS FOR MEASURING IN VIVO CYTOKINE PRODUCTION

This application is based on U.S. Provisional Patent Application Ser. No. 60/061,167, Finkelman and Morris, filed Oct. 6, 1997.

This invention was made in part with Government support under Grant Nos. R01AI35987 and R01AI37180 awarded by the National Institutes of Health. The Government may have certain rights in this invention.

FIELD OF THE INVENTION

The invention relates to methods for monitoring immunological function in a human or animal. More particularly, the present invention relates to accurately measuring the production of cytokines in vivo.

BACKGROUND OF THE INVENTION

There have been many attempts to measure endogenous cytokines in blood and other body fluids. However, in reviewing these reports, it is apparent that there is wide variation in the reported results with regard to cytokine concentration in the blood and to fluctuations of cytokine concentration in the blood. Measurement of cytokine production in vivo is an important part of many experimental and therapeutic studies. Interpretation of results has been difficult, however, for several reasons:

1. Studies that examine cytokine secretion ex vivo are relatively easy to perform, but may not reflect cytokine production in vivo.
2. Cytokine levels in serum or other biological fluids can be measured in some cases; however, levels are often negligible because many cytokines have a very short in vivo half-life. In addition, increased absorption of cytokines by receptors on activated cells may accelerate catabolism of cytokines, so that serum levels will not correlate directly with secretion.
3. Cytokine mRNA levels can be measured directly after removal of cells or organs, and presumably, accurately reflect in vivo cytokine mRNA levels; however, protein production and secretion doesn't always vary directly with mRNA levels.
4. Cytokine-containing cells have been identified by staining procedures; however, the small number of such cells in the absence of in vitro restimulation and subjectivity in identifying such cells by staining techniques place limits on the usefulness of these techniques. In addition, it is not known if all cytokine-secreting cells have identical levels of stored, intracellular cytokine, so that intensity of staining and rate of secretion do not necessarily correlate directly.
5. ELISPOT assays for cytokine-secreting cells can be performed on cells right after they are removed from an animal; however, enumeration of cytokine-secreting cells with this technique is somewhat subjective, and this technique may detect only those cells that secrete the largest amount of cytokine, may favor selective detection of those cells that contain stores of a preformed cytokine, and, even if the assay involves only a short incubation period, may not reflect in vivo cytokine production because of the disruption of normal architecture, the possibility that some activated cells may be difficult to remove intact from organs, the possibility that the trauma of preparing single cell suspensions may modify cytokine secretion, etc.

Many reports indicate that cytokines (i.e., IL-2) are not detectable in normal subjects using immunoassays. Cytokines are difficult to measure in serum for several reasons: 1) rapid renal excretion; 2) catabolism; 3) cellular utilization; and 4) binding to molecules, such as soluble receptors that mask the cytokine active site.

It would be of great benefit if one could easily, accurately and reproducibly measure in vivo cytokine production by sampling body fluids, such as blood. This would create a useful window not only into the immune system but into a myriad of physiologically interacting processes. Such a tool would be useful in a variety of settings, allowing the collection of data of importance to basic medical sciences, clinical medicine, epidemiology and the forensic sciences.

U.S. Pat. No. 4,486,530, David et aL, issued Dec. 4, 1984, discloses a "Two-site" or "sandwich" immunometric assay technique for determination of the presence and/or concentration of antigenic substances in fluids using monoclonal antibodies. These are described and compared to conventional assays using polyclonal antibodies. Also described are inhibition assays using complexes of antigens with a monoclonal antibody. This reference discloses methods for detecting and/or determining the concentration of antigenic substances in fluids such as serum.

U.S. Pat. No. 5,587,294, Tamarkin et al., issued Dec. 24, 1996, discloses methods for measuring endogenous cytokines in blood. The method accurately measures the cytokines in the blood in the presence of substances that bind the cytokines thereby causing the measurement of the cytokines by conventional methods to give inaccurate results. The Tamarkin et aL patent also describes the non-invasive measurement of cytokines in biological fluids such as saliva and nasal secretions. Finally, the procedure described in Tamarkin et al., allows one to monitor the level of cytokines in the blood during treatment of a human or animal with cytokines.

Others have shown the prolongation of in vivo effects of exogenous cytokines by injection of cytokine--anti-cytokine antibody complexes. (*J. ImmunoL* 151:1235, 1993). This reference describes a technique whereby animals are injected with preformed complexes of a cytokine and an anticytokine MAb. The antibody acts as a carrier protein for the cytokine, slowly dissociating and thereby increasing the period of time during which active cytokine is present in an animal. This paper does not mention the use of this technique for determining cytokine production in vivo. It does reference other publications that mention that endogenously produced anti-cytokine antibodies may enhance the half-life and activity of endogenously produced cytokines in vivo; however, these papers also did not mention this as a possible technique for measuring endogenous cytokine production. The reference does not disclose the idea of labeling an injected anticytokine antibody to facilitate detection of cytokine/anti-cytokine antibody complex.

U.S. Pat. No. 5,612,034, Pouletty et al., issued Mar. 18, 1997, provides first and second compounds, where the first compound is administered to a mammalian host into blood for covalent bonding to blood components, where the components have an extended lifetime in the blood stream. The first compound comprises an active functionality and an agent of interest or a first binding entity. A second compound may be subsequently administered to the patient, which comprises a second binding entity, complementary to the first binding entity and an agent of interest. By virtue of binding to long-lived blood components, the half-life of the agent of interest is greatly extended in vivo.

It would be of great benefit if one could easily, accurately and reproducibly measure the concentrations of various endogenous cytokines in blood in vivo. This would provide information not only of the immune system but of a variety of physiologically interacting processes. Such tools would be useful in a variety of settings, allowing the collection of data of importance to basic medical sciences, clinical medicine, epidemiology and the forensic sciences.

What is needed is a reliable method of measuring endogenous cytokine production by sampling blood, which is only minimally affected by cytokine catabolism, utilization, excretion, or binding to endogenous cytokine binding proteins.

SUMMARY OF THE INVENTION

The present invention provides methods for measuring the endogenous level of a target analyte which may be a hormone, drug or other analyte in a human or animal. The target analyte is preferably a macromolecule, more preferably a protein, and most preferably a cytokine.

The present invention is an immunoassay for use in detecting and monitoring endogenous cytokine production. Prior methods have been unable to accurately measure cytokine production because of rapid excretion, catabolism, and utilization of cytokines as well as the binding of cytokines to endogenous cytokine binding proteins, which can interfere with detection. The present invention obviates all of these difficulties.

The present invention provides the capability of measuring "basal," as well as "stimulated," cytokine production. The present invention provides a new tool for monitoring these chemical communication signals and their dysregulation in the face of challenges by pathogens, chemicals, therapeutics as well as by biobehavioral factors.

The present invention is especially useful in measuring proteins secreted into extracellular fluid, including blood, and includes, but is not limited to, proteins from the group consisting of interleukins 1 through 18, interferon-alpha, interferon-beta, interferon-gamma, lymphotoxin, and tumor necrosis factor-alpha. It is contemplated that the present invention will be useful in detecting and quantifying other cytokine-like molecules in the blood that have not yet been characterized.

In general, the present invention provides a method of measuring the production of a target analyte of interest in a human or animal, comprising the steps of:
  a. injecting a human or animal with an appropriate amount of targeting moiety capable of binding specifically to the target analyte;
  b. allowing the targeting moiety to circulate through the injected human or animal for a time sufficient to bind to the target analyte of interest and form a targeting moiety: target analyte conjugate;
  c. obtaining a sample of body fluid from the human or animal without dissociation of the target analyte from targeting moiety;
  d. combining the sample of body fluid with a capture moiety capable of binding specifically to the analyte determinants of the targeting moiety: target analyte conjugate;
  e. incubating the assay mixture to allow the immobilized capture moiety to bind specifically to either the target analyte or the labeled targeting moiety;
  f. removing unbound targeting moiety and target analyte from the capture moiety;
  g. detecting the bound conjugate on the capture moiety; and
  h. determining the amount of the target analyte in the sample.

The body fluid sampled is generally saliva, blood or extracellular fluid. The targeting moiety used is preferably antibodies, soluble receptors, paratopic molecules, recombinant molecules with binding sites for the target analyte, or fragments thereof. The targeting moiety is preferably an antibody and most preferably a polyclonal antibody which recognizes many epitopes on the target analyte.

Generally, the targeting moiety is detectably labeled through the use of a labels which are preferably radioisotopes, affinity labels, enzymatic labels, or fluorescent labels. Preferably, the targeting moiety is labeled by linking the targeting moiety to a label which label can then be bound to a binding partner which is conjugated to an enzyme. More preferably, the label is a small molecule happen. Most preferably, the hapten is biotin.

The present invention also provides for reagent kits useful in performing the methods disclosed, providing:
  (a) a first reagent containing a labeled targeting moiety specific for the target analyte and capable of forming a conjugate with the target analyte;
  (b) a second reagent separated from said first reagent which contains a capture moiety for said conjugate; and
  (c) a third reagent separated from said first and second reagents which contains a standard for the analyte.

Preferably, the targeting moiety is an antibody and the capture moiety is an antibody. More preferably, these antibodies are polyclonal. Also, it is preferred that the capture antibodies are immobilized on a solid support The present invention also provides reagent kits useful in performing the disclosed methods, comprising: (a) a first container having paratopic molecules that immunoreact with a target analyte, and are operatively linked to an enzyme indicating means; (b) a second container having paratopic molecules that immunoreact with the target analyte at a site different from the first paratropic molecules but are not in the first container; and (c) one or more other containers comprising one or more of the following: a sample reservoir, a solid phase support, wash reagents, reagents capable of detecting presence of bound antibody from the second container, or reagents capable of amplifying the indication means.

Preferably, the paratopic molecules are detectably labeled through the use of a label selected from the group consisting of radioisotopes, affinity labels, enzymatic labels, and fluorescent labels. Most preferably, the paratopic molecules are detectably labeled through the use of fluorescent labeling agents are fluorochromes e.g., fluorescein isocyanate (FIC), fluorescein isothiocyanate (FITC), 5-dimethylamine-1-naphthalenesulfony chloride (DANSC), tetramethylrhodamine isothiocyanate (TRITC), lissamine, rhodamine 8200 or sulphonyl chloride (RB 200 SC).

In another embodiment, the present invention is directed to a method for monitoring immunological activity of a subject comprising measuring the concentration of a cytokine.

Accordingly, it is an object of the present invention to provide a method for accurately measuring the endogenous production of cytokines in humans or animals by sampling their blood.

Yet another object of the present invention is to provide a method by which the production of cytokines can be correlated to a pathological condition.

It is yet another object of the present invention to provide a method for evaluating and measuring cytokine production in response to behavioral perturbations.

It is a further object of the present invention to provide a method for evaluating cytokine production as a response to chemical, viral, parasite or bacterial challenges.

It is yet another object of the present invention to provide a method for ffi monitoring cytokine production during the course of an identified disease.

These and other objects, features and advantages of the present invention will become apparent after a review of the following detailed description of the disclosed embodiments and the appended claims.

DETAILED DESCRIPTION OF THE INVENTION

Prior to setting forth the invention, it may be helpful to set forth definitions of certain terms to be used within the disclosure.

The term "antibody" refers to a molecule that is a member of a family of proteins called irununoglobulins that can specifically combine with an antigen. Such an antibody combines with its antigen by a specific immunologic binding interaction between the antigenic determinant of the antigen and the antibody combining site of the antibody.

An "antibody combining site" is that structural portion of an antibody molecule comprised of heavy and light chain variable and hypervariable regions that specifically binds antigen. Using the nomenclature of Jeme, *Ann. Immunol.*, 125:373–389 (1974), an antibody combining site is usually referred to herein as a "paratope."

Antibody combining site-containing (paratope-containing) polypeptide portions of antibodies are those portions of antibody molecules that contain the paratope and bind to an antigen, and include, for example, the Fab, Fab', F(ab')2 and F(v) portions of the antibodies. Intact antibodies are preferred, and are utilized as illustrative of the monoclonal ligand molecules of this invention.

The word "antigen" has been used historically to designate an entity that is bound by an antibody, and also to designate the entity that induces the production of the antibody. More current usage limits the meaning of antigen to that entity bound by an antibody, whereas the word "immunogen" is used for the entity that induces antibody production. Where an entity discussed herein is both immunogenic and antigenic, it will generally be termed an antigen.

The phrase "antigenic determinant" refers to the actual structural portion of the antigen that is immunologically bound by an antibody combining site. The Jerne nomenclature redefines an antigenic determinant as an "epitope."

"ELISA" refers to an enzyme-linked immunosorbent assay that employs an antigen or antibody bound to a solid phase and an enzyme-antibody or enzyme-antigen conjugate to detect and quantify the amount of antigen or antibody present in a sample. A description of the ELISA technique is found in U.S. Pat. Nos. 3,654,090, issued Apr. 4, 1972;3; 850,752, issued Nov. 26, 1974; and 4,016,043, issued Apr. 5, 1977, all to Schuurs, et al., which are incorporated herein by reference.

"Enzyme" refers to a protein capable of accelerating or producing by catalytic action some change in a substrate for which it is often specific. "Enzyme activity" refers to a measurement of the catalytic capabilities of an enzyme to convert substrate to product usually expressed in units per weight of sample tested an "Immunoreactant" as used herein refers to the product of an immunological reaction; i.e., that entity produced when an antigen is immunologically bound by an antibody or a molecule containing a paratope.

As used herein, the terms "label" and "indicating means" in their various grainmatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodarnine isothiocyanate (TRITC), lissamine, rhodamine 8200 sulphonyl chloride (RD 200 SC) and the like.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Paratopic molecules when linked to enzyme labels are also sometimes referred to herein as being enzyme-linked paratopic molecules.

As used herein, a "targeting moiety or reagent" is a molecule that binds to a defined soluble molecular target. The targeting moiety may bind a receptor, a cytokine, a hormone, a drug, or other soluble molecule. Antibody is used throughout the specification as a protypical example of a targeting moiety.

As used herein, a "ligand/anti-ligand pair" is a complementary/anticomplementary set of molecules that demonstrate specific binding, generally of relatively high affinity. Exemplary ligand/anti-ligand pairs include hapten/antibody, ligand/receptor, and biotin/avidin. Biotin/avidin is used throughout the specification as a prototypical example of a ligand/anti-ligand pair.

As defined herein, an "anti-ligand" demonstrates high affinity, bivalent or univalent binding of the complementary ligand. Preferably, the anti-ligand is large enough to avoid rapid renal clearance, and has an in vivo half-life greater than the ligand The anti-ligand should not cause the production of large ligand/anti-ligand aggregates which could be removed rapidly from blood or lymph by the reticuloendothelial system.

As defined herein, "avidin" includes avidin, streptavidin and derivatives and m_ analogs thereof that are capable of high affinity, multivalent or univalent binding of biotin. As defined herein, a "ligand" is a relatively small, soluble molecule that exhibits rapid serum, blood and/or whole body clearance when administered intravenously in an animal or human.

As used herein, the term "cytokine" is defined as growvth, differentiation or chemotropic factors secreted by immune or other cells, whose action is on cells of the immune system, such as, but not limited to, T-cells, B-cells, NK cells and macrophages or other cell types, such as endothelial cells, hematopoitic cells, etc. Representative cytokines include, but are not limited to, the group consisting of interleukin 1 alpha, interleukin-1 beta, interleukin-2, interleukin-3, interleukin-4, interleukin-6, interferonalpha, interferon-gamma, tumor necrosis factor-alpha, and growth factors, such as TGF-beta, GM-CSF, NGF, EGF. The term "EIA" means any immunoassay utilizing enzymes as the label. The term "endogenous cytokines" as used herein, means cytokines that are produced in vivo. The term includes prohormones which are larger molecular weight forms of cytokines which have not yet undergone post-transcriptional modification.

The present invention provides methods for measuring the level of a target analyte which may be a hormone, drug or other analyte in a human or animal. The target analyte is preferably a macromolecule, more preferably a protein, and most preferably a cytokine. Preferably, the method prevents cytokine destruction, utilization, and excretion so that cytokines will accumulate in extracellular fluids, including blood. According to the present invention, cytokine-type proteins can be accurately measured in the blood even in the presence of cytokine binding proteins which mask the cytokine activity in conventional assays.

In general, the present invention provides a method of measuring the production of a target analyte of interest in a human or animal, comprising the steps of:

a. injecting a human or animal with an appropriate amount of targeting moiety capable of binding specifically to the target analyte;

b. allowing the targeting moiety to circulate through the injected human or animal for a time sufficient to bind to the target analyte of interest and form a targeting moiety: target analyte conjugate;

c. obtaining a sample of body fluid from the human or animal without dissociation of the target analyte from targeting moiety;

d. combining the sample of body fluid with a capture moiety capable of binding specifically to the analyte determinants of the targeting moiety: target analyte conjugate;

e. incubating the assay mixture to allow the immobilized capture moiety to bind specifically to either the target analyte or the labeled targeting moiety;

f. removing unbound targeting moiety and target analyte from the capture moiety;

g. detecting the bound conjugate on the capture moiety; and h. determining the amount of the target analyte in the sample.

The body fluid sampled is generally saliva, blood or extracellular fluid. The targeting moiety used is preferably antibodies, soluble receptors, paratopic molecules, recombinant molecules with binding sites for the target analyte, or fragments thereof. The targeting moiety is preferably an antibody and most preferably a polyclonal antibody which recognizes many epitopes on the target analyte.

Generally, the targeting moiety is detectably labeled through the use of a labels which are preferably radioisotopes, affinity labels, enzymatic labels, or fluorescent labels. Preferably, the targeting moiety is labeled by linking the targeting moiety to a label which label can then be bound to a binding partner which is conjugated to an enzyme. More preferably, the label is a small molecule hapten. Most preferably, the hapten is biotin.

These methods are particularly useful for monitoring immunological activity in a subject. Such monitoring may be used in (1) subjects undergoing cytokine immunotherapy, or other forms of therapy, (2) patients with immunological disorders in which cytokine production is abnormal, (3) individuals being studied for the effects of behavioral influences on immune function, and the like. The methods of the present invention may be used to detect the presence or measure the concentration or level of any of a number of known interleukins, interferons, chemokines, lymphokines, growth factors, colony stimulating factors, lymphotoxins, and tumor necrosis factors. Preferably, the cytokine is interleukin-1, interleukin-2, interleukin-3, interleukin-4, interleukin-5, interleukin-6, interleukin-7, interleukin-8, interleukin-9, interleukin-10, interleukin-11, interleukin-12, interleukin- 13, interleukin-14, interleukin-15, interleukin-16, interleukin17, interleukin-18, interferon-alpha, interferon-gamma, tumor necrosis factor-alpha, lymphotoxin, and growth factors, such as TGF-beta, GM-CSF, NGF, and EGF.

Conventional immunoassays are well known in the art (see, U.S. Pat. No. 4,228,237, Hevey et al., issued Oct. 14, 1980; U.S. Pat. No. 4,298,685, Parikh et al., issued Nov. 3, 1981, which are hereby incorporated by reference).

The present invention includes novel forms of the enzyme linked immunosorbent assay (ELISA) (see also Plebani et al., J. IMMUNOL. METH. 90:241 (1986)) to measure ehormones, drugs, growth factors and other analytes in blood without the need to separate out interfering factors. The manner by which an unknown analyte, such as a cytokine, is detected is similar to that of a radioimmunoassay.

The methods of the present invention may be used for evaluating in vivo cytokine production through the in vivo capture of secreting cytokines by cytokine-binding reagents, followed by in vitro measurement of serum levels of captured cytokine. The method of the present invention for measuring the level of an analyte in blood typically comprises injecting a human or animal with a targeting molecule and allowing the targeting molecule to circulate throughout the body.

The "targeting moiety" of the present invention binds to a defined "target analyte," e.g., a cytokine or lymphokine, such as IL-2. Preferred targeting moieties useful in this regard include antibody and antibody fragments, and soluble analyte receptors. Analogs of the above-listed targeting moieties that retain the capacity to bind to a defined analyte may also be used within the claimed invention. In addition, synthetic targeting moieties may be designed.

In the circulation, the targeting molecule is brought in proximity to the target analyte, the targeting moiety binds the circulating target analyte and produces a targeting moiety: analyte conjugate. Because, at that point, the target analyte is attached to a slowly clearing targeting moiety (e.g., antibody, antibody fragment, soluble cytokine receptor, fusion protein, or other slowly clearing anti-ligand moiety), this technique decreases clearing of the active target analyte.

After a set period of time, typically from about 1 hour to about 72 hours, a blood sample is taken from the host and serum prepared. A second targeting moiety, which recognizes a site on the analyte that is distinct from the site bound by the injected targeting moiety, is used to bind the targeting moiety: analyte conjugates. The second targeting moiety is typically bound to a solid-phase support, e.g., microtiter plate wells. Preferably, serial or standard dilutions of the serum, prepared from the host blood, are added to the solid support-bound second targeting moiety to bind and contain the targeting moiety: analyte conjugate.

In one aspect of the present invention, the targeting moiety is administered in vivo with the targeting moiety labeled with a ligand, e.g., biotin, that can then be bound by another molecule, an anti-ligand, e.g., avidin. Although a variety of ligand/anti-ligand pairs may be suitable for use within the claimed invention, a preferred ligand/anti-ligand pair is biotinlavidin or biotin/streptavidin.

Ligands suitable for use within the present invention include biotin, haptens, epitopes and analogs and derivatives thereof. Useful complementary anti-ligands include avidin (for biotin) and antibody, fragments or analogs thereof, including mimetics (for haptens and epitopes).

In another aspect of the present invention, a targeting moiety is administered in vivo with the targeting moiety itself capable of being bound by another molecule. In this embodiment, a targeting moiety is typically an antibody of a species different than the host. The foreign antibody is then capable of being bound by a specific anti-antibody antibody.

In one embodiment, the methods of the present invention make use of the ability of a neutralizing antibody to a cytokine, when injected into a person or experimental animal, to bind that cytokine and prevent its catabolism, excretion, or binding to a cytokine receptor. This causes the cytokine, which may normally have a very short in vivo half life, to accumulate in vivo as a cytokine/anti-cytokine antibody complex.

If the anti-cytokine antibody is either labeled with a molecule that can be bound by another molecule (e.g.; biotin, which is bound by avidin or streptavidin), or is itself capable of being bound by another molecule (e.g., a rat anti-cytokine antibody could be bound by an anti-rat immunoglobulin antibody), and the cytokine can also be bound by an antibody that recognizes a site distinct on the cytokine molecule from the site bound by the injected, neutralizing antibody, then the concentration of the cytokine/anti-cytokine complex in serum or other biological fluid can easily be assayed by a modified ELISA.

To measure in vivo analyte production over a given period of time, experimental animals are injected with a analyte-binding molecule, such as an anti-analyte monoclonal antibody (MAb) or soluble analyte receptor that has a longer in vivo half-life than the analyte itself, and which is labeled with an additional molecule, such as biotin.

In the preferred iteration of this technique, the analyte-binding molecule binds the analyte in a way that prevents it from binding to a cellular analyte receptor; so that cellular binding of the analyte will not decrease its serum level; however, in an alternative iteration, this technique could also be used with a analyte-binding molecule that does not prevent binding of the analyte to a cellular receptor. The analyte-binding molecule needs to be injected in sufficient quantity that a measurable fraction of secreted analyte is bound by the analyte-binding molecule; and must have a sufficient avidity for the analyte that much of the analyte bound by the analyte-binding molecule will remain bound in vivo by the analyte-binding molecule for a period of hours to days, and during a subsequent in vitro assay.

Following injection and distribution of the analyte-binding molecule, secreted analyte will be bound by this molecule and form a soluble complex, which will accumulate in blood and in other sites to which the analyte-binding molecule has distributed. After a period of time, the animal is bled. The concentration of the analyte, or analyte/analyte-binding molecule complex in the blood can then be determined by an ELISA, or similar assay. The ELISA will use wells coated with a analyte-binding molecule that binds the analyte at a site different from that bound by the labeled analyte-binding molecule that was injected into the animal, so that the binding of the analyte by the plate-bound analyte-binding molecule will not be inhibited by the binding of the analyte by the labeled analyte-binding molecule that had been injected into the animal (e.g.; an in vivo-generated complex of labeled analyte-binding molecule and analyte will be able to bind efficiently to the analyte-binding molecule used to coat the ELISA plate wells).

Binding of the analyte/aabeled analyte-binding molecule complex by the second analyte-binding molecule that was used to coat the ELISA plate well is detected by an enzyme-linked molecule that binds to the analyte-binding molecule that was injected into the animal (e.g.; if a biotin-labeled analyte-binding molecule had been used, the binding of the analyte/biotin-labeled analyte-binding molecule complex to the well-bound second analyte-binding molecule could be detected by the binding of an enzyme linked to avidin or streptavidin, followed by a substrate that generates a colored reaction product when acted on by the enzyme). The concentration of the colored reaction product in the fluid filling the well can then be detected by absorption spectroscopy, as in any standard ELISA. The concentration of colored reaction product in the ELISA well should be directly proportional to the amount of analyte that was secreted in vivo, and that accumulated in vivo as the analyte/analyte-binding molecule complex. As in any ELISA, it is anticipated that this relationship between the concentration of the analyte/analyte-binding molecule complex and the concentration of the colored reaction product will be linear only within a particular range, so that ELISA analysis of serial dilutions of the fluid containing the complex may need to be performed to determine the concentration of the complex.

This technique can be used to measure cytokine production in any animal, including humans, and can even be applied in vitro to keep secreted cytokine from being utilized. It can be used with injected cytokine-binding molecules that have any label, including a label intrinsic to the molecule itself (e.g.; a rabbit anti-cytokine antibody could be injected that had no extrinsic label, if it were later recognized in an ELISA by an enzyme-anti-rabbit Ig antibody complex). The detection of cytokine/cytokine-binding molecule complex can be performed with an ELISA, radioimrnmunoassay, an assay in which the reaction product is detected by fluorimetry rather than absorbance, or by any assay system that uses any kind of label to detect the concentration of complex in a solution. This technique can be used to measure molecules other than cytokines, that are secreted, shed, or otherwise produced in vivo, including, but not limited to, hormones, peptides, and drug metabolism products.

The major innovation of this technique is that it protects/preserves molecules that are produced in vivo that would ordinarily have a short in vivo half-life by binding them to a molecule that has a longer in vivo half-life, that can itself be identified in an ELISA or similar assay. Because only the complex of analyte and labeled analyte-binding molecule would be detected in the in vitro assay, a sufficient quantity of labeled analyteAd binding molecule could be injected into an animal to assure that a measurable fraction of the secreted analyte would bind and remain bound to a labeled analyte-binding molecule.

In a preferred embodiment of the present invention, after collection of serum, an antibody, either a monoclonal or a polyclonal anti-cytokine, is adsorbed to a solid phase support or carrier, preferably the wells of a polystyrene microtiter plate. This antibody, known as a "capture antibody," is then used to bind the targeting moiety: analyte conjugate, e.g., biotinylated anti-IL-1 antibody:IL-1 or the standard.

After appropriate washing steps, an enzyme-conjugated binding partner for the label, for example, streptavidin or an anti-biotin antibody, is incubated with the antibody-analyte complex, allowing the enzyme to be bound to the complex. After removal of any unbound enzyme-conjugated binding partner, a chromogenic enzyme substrate is added. The bound enzyme converts the substrate to a colored product which can be detected by calorimetric means. The amount of color that develops per unit time is directly proportional to the amount of analyte present in the sample. As the concentration of analyte, for example IL-1, increases, the amount of color generated increases.

In a preferred form of the assay, during the first two hours, the capture antibody, a monoclonal or polyclonal anti-cytokine antibody, is adsorbed to the wells of a 96-well immunoplate. During the next two hours, unbound antibody is washed off the plate followed by addition of either standards or unknowns, as well as a specific amount of labeled analyte, preferably biotinylated analyte. The amount of labeled cytokine which has bound is then detected by the addition of the binding partner, preferably streptavidin, conjugated to an enzyme, preferably alkaline phosphatase, followed by addition of the chromogenic substrate, preferably p-nitrophenyl phosphate. The resultant color is then read as absorbence (or optical density, O.D.) at an appropriate wavelength, e.g., 405 nm for p-dinitrophenol. The color can be read using a colorimeter, such as an ELISA plate reader, at several time points, for example at about 0.5 hours and at about 24 hours.

The term "solid phase support" means any support capable of binding antigen or antibodies. Well-known supports, or carriers, include, but are not limited to, polystyrene, polypropylene, polyethylene, glass, dextran, nylon, amylases, natural and modified celluloses, polyacrylamides, agaroses, and magnetite. The support material may have virtually any structural configuration so long as on its surface, the antigen is capable of binding to an antibody. Thus, the support configuration may be spherical, as in a bead, or cylindrical, as in the inside surface of a test tube, or the external surface of a rod. Alternatively, the surface may be flat such as a sheet, test strip, etc. A preferred carrier is the bottom and sides of a polystyrene microtiter plate well. Those skilled in the art will know many other suitable carriers for binding antibody or antigen, or will be able to ascertain the same by use of routine experimentation.

A preferred means of labeling the analyte, e.g., the cytokine (or anti-cytokine antibody) is by linking to it a label which can be bound to a binding partner which is conjugated to an enzyme in an EIA. This enzyme, in turn, when later exposed to its substrate, will react with the substrate in such a manner as to produce a chemical moiety which can be detected, by spectrophotometric, fluorometric or by visual means. Enzymes which are useful in the EIA method of the present invention include, but are not limited to, alkaline phosphatase, glucose oxidase, beta -galactosidase, malate dehydrogenase, staphylococcal nuclease, delta-5-steroid isomerase, yeast alcohol dehydrogenase, alphaglycerophosphate dehydrogenase, triose phosphate isomerase, horseradish peroxidase, asparaginase, ribonuclease, urease, catalase, glucose-6-phosphate dehydrogenase, glucoamylase and acetylcholinesterase.

It is also possible to label the analyte-binding moiety with a fluorescent compound. When the fluorescent labeled bound analyte is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The analyte-binding moiety can also be labeled with fluorescence emitting metals such as $_{152}Eu$, or others of the lanthanide series. These metals can be attached to the analyte or antibody using such metal chelating groups as diethylene-triaminepentaacetic acid (DTPA) or ethylenediaminetetraacetic acid (EDTA).

The analyte or antibody also can be labeled by coupling it to a chemiluminescent compound. The presence of the chemiluminescent-tagged bound molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the analyte or antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In addition to use of the enzyme immunoassay, the method of the present invention can measure the level of a cytokine using any of a variety of other immunoassays. For example, by radioactively labeling the cytokine (or the cytokin-especific antibodies or antibody fragments or molecules, such as streptavidin, that bind to the cytokine-specific antibodies), it is possible to detect the cytokine through the use of a radioimmunoassay (RIA). A good description of RIA may be found in Weintraub, B., PRINCIPLES OF RADIOIMMUNOASSAYS, Seventh Training Course on Radioligand Assay Techniques, The Endocrine Society, pp. 1–5, 46–49 and 68–78 (March, 1986). See also: Work, T. S. et al., LABORATORY TECHNIQUES AND BIOCHEMISTRY IN MOLECULAR BIOLOGY, North Holland Publishing Company, New York (1978).

The radioactive isotope can be detected by such means as the use of a gamma counter or a scintillation counter or by autoradiography. Isotopes which are particularly useful for the purpose of the present invention are $^3H$, $^{125}I$, $^{132}I$ $^{35}S$ $^{14}C$ and preferably $^{125}I$.

The binding activity of a given lot of anti-cytokine antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

Detection of the labeled antibody or binding partner for the labeled analyte may be accomplished by a scintillation counter, for example, if the detectable label is a radioactive gamma emitter, or by a fluorometer, for example, if the label is a fluorescent material. In the case of an enzyme label and a chromogenic substrate, the detection can be accomplished by calorimetric methods. Detection may also be accomplished by visual comparison of the extent of enzymatic reaction of a substrate in comparison with similarly prepared standards.

An example of this technique would be the detection of the cytokine interleukin-4 (IL-4) in immunostimulated mice.

Such mice could be injected with biotin-labeled MAb 1DII.2, which binds to mouse IL-4 and blocks its binding to cellular IL4 receptors. After a fixed period of time, mice would be bled and serum prepared. Serum would be assayed for IL-4/biotin-1D11.2 complex by ELISA, using microtiter plate wells coated with 24G2.3, a MAb that recognizes an IL-4 epitope distinct from that bound by 1D11.2. Following addition of serial dilutions of serum to 24 G2.3-coated, blocked, microtiter plate wells, complex binding would be detected by sequential addition of alkaline phosphatase-streptavidin and a chromagenic substrate for alkaline phosphatase. The colored reaction product would be detected with a spectrophotometric ELISA plate reader, and either relative or absolute concentrations of ILA could be calculated from the results, with reference to an IL-4 standard.

For example, if the cytokine is IL-4, the injected anti-cytokine antibody is biotinlabeled ID11.2, (a monoclonal antibody that neutralizes IL-4), and the second, microtiter plate-bound anti-IL-4 antibody is 24 G2.3, (which binds to a site on the IL-4 molecule that is not blocked when IL-4 is bound by biotin-1D11.2), the in vivo secretion of IL4 in a mouse over a four hour period could be measured by:
 a) injecting the mouse with 10 μg of biotin-1D11.2, a quantity determined experimentally;
 b) waiting four hours;
 c) bleeding the mouse and preparing serum from the blood;
 d) adding sequential dilutions of the serum to microtiter plate wells that are coated with 24 G2.3;
 e) washing the wells after an incubation period and then adding alkaline phosphatase-streptavidin to the wells;
 f) washing the wells after an incubation period and then adding an alkaline phosphatase substrate to the wells that becomes colored when a phosphate group is cleaved from the substrate; and
 g) determining the concentration of the colored substrate that has been generated after a fixed period of time with an ELISA reader (absorption spectroscopy). Applications of this technique may vary in:
 a) the secreted compound that is being measured (this could include hormones, drug metabolites, etc., as well as cytokines)
 b) the label that is applied to the injected antibody;
 c) the use of a molecule other than an antibody, such as a soluble receptor, to bind the secreted cytokine;
 d) the route by which the cytokine-binding molecule is injected into the animal; and
 e) the details of the ELISA, radioimmunoassay, or related assay that is used to detect the in vivo-generated complex.

In addition, this technique could be used in a cell culture system instead of in vivo (i.e.; the labeled anti-cytokine antibody would be added to the cell culture instead of being injected into the animal and complex levels in culture supernatant would be measured). The main advantages are that this technique allows:
 the accumulation in serum of a secreted or shed biological material that normally has a short in vivo half-life. The use of a labeled antibody or other molecule that binds the biological material greatly facilitates the measurement of the biological material in serum. No other technique has been described that allows quantitation of the amount of a biological material that has been secreted over a fixed, definable period of time in vivo.
 (2) Repeated measurements of cytokine production over time to be made in individual humans or experimental animals; and
 (3) Measurement of cytokine production that is influenced little, if any, by the presence of endogenously produced soluble cytokine receptors.

The present invention also provides test kits for use with the methods of the present invention. The kit of the present invention is useful for measuring analytes, e.g., cytokines, in a body fluid, preferably blood. The kit is preferably assembled under Quality Assurance procedures applicable to in vitro diagnostic products licensed as medical devices by the Food and Drug Administration. Preferably, the body fluid sample is provided as a known amount of blood or a blood derived product such as serum or plasma.

The present invention also provides for reagent kits useful in performing the methods disclosed, providing:
 (a) a first reagent containing a labeled targeting moiety specific for the target analyte and capable of forming a conjugate with the target analyte;
 (b) a second reagent separated from said first reagent which contains a capture moiety for said conjugate; and
 (c) a third reagent separated from said first and second reagents which contains a standard for the analyte.

Preferably, the targeting moiety is an antibody and the capture moiety is an antibody. More preferably, these antibodies are polyclonal. Also, it is preferred that the capture antibodies are immobilized on a solid support The present invention also provides reagent kits usefull in performing the disclosed methods, comprising: (a) a first container having paratopic molecules that immunoreact with a target analyte, and are operatively linked to an enzyme indicating means; (b) a second container having paratopic molecules that imrnunoreact with the target analyte at a site different from the first paratropic molecules but are not in the first container; and (c) one or more other containers comprising one or more of the following: a sample reservoir, a solid phase support, wash reagents, reagents capable of detecting presence of bound antibody from the second container, or reagents capable of arnplifing the indication means.

In one embodiment, the kit comprises:
 (a) a container containing a labeled targeting moiety specific for the target analyte to be measured, e.g., cytokine, and capable of forming a conjugate with the target analyte;
 (b) a second container containing purified target analyte in labeled form; and
 (c) a third container containing a capture moiety for said conjugate.

The above kit preferably further comprises:
 (d) means for collecting biological fluid secretion;
 (e) a solid phase carrier.

In a preferred format, a kit contains enough reagents to perform analysis of several unknowns (in duplicate). In another embodiment, the kit of the present invention comprises:
 (1) a labeled targeting moiety, e.g., antibody, specific for the analyte, e.g., a cytokine, to be measured;
 (2) a capture moiety specific for a determinant site on the analyte different from the determinant site recognized by the targeting moiety;
 (3) standard target analyte to serve as the assay standard; and
 (4) enzyme conjugated binding partner for the label on the labeled targeting moiety. The kit may optionally contain:
 (5) chromogenic substrate for the enzyme;

(6) coating buffer;
(7) standard diluent;
(8) substrate buffer;
(9) wash buffer; and
(10) 96-well microtiter plates. In another embodiment, the kit of the present invention comprises:
(1) a targeting moiety specific for the analyte, e.g., a cytokine, to be measured;
(2) a labeled antibody capable of binding specifically to the targeting moiety;
(3) a capture moiety specific for a determinant site on the analyte different from the determinant site recognized by the targeting moiety;
(4) standard target analyte to serve as the assay standard; and
(5) enzyme conjugated binding partner for the label on the labeled antibody capable of binding specifically to the targeting moiety.

The kit may optionally contain:
(6) chromogenic substrate for the enzyme;
(7) coating buffer;
(8) standard diluent;
(9) substrate buffer;
(10) wash buffer;
(11) 96-well microtiter plates; and
(12) 96-well microtiter plates coated with the capture moiety.

Such a kit may comprise a carrier being compartmentalized to receive in close confinement therewith one or more containers such as vials, tubes, and the like, each of said containers comprising the separate elements of the immunoassay.

For example, there may be a container containing the capture moiety in fluid phase or alternatively, already immobilized on a solid phase support. A firther container contains labeled (e.g., biotin—or enzyme-conjugated) targeting moieties or antibodies in solution. Further containers may contain standards comprising serial dilutions of the cytokine to be detected. The standard solutions of the cytokine are used to prepare a standard curve with the concentration of the cytokine plotted on the abscissa and the detection signal on the ordinate. The results obtained from a sample, e.g. blood, containing the cytokine may be interpolated from such a plot to give the concentration of the cytokine.

In the above kit, the analyte to be measured may be any of a number of known interleukins, interferons chemokines, iymphokines, growth factors, colony stimulating factors, lymphotoxins, and tumor necrosis factors. Preferably, the cytokine is interleukin1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interferonalpha, interferon-gamma, tumor necrosis factor-alpha, TGF-beta, GM-CSF, NGF, and EGF.

In one embodiment of the above kit, a preferred label for the cytokine is biotin and a preferred second binding partner is streptavidin. In a preferred embodiment, the targeting moiety is an antibody specific for the analyte, e.g., cytokine, the second binding partner is an enzyme-conjugated binding partner, preferably enzyme conjugated-streptavidin. Preferably, the enzyme is alkaline phosphatase. The kit may additionally comprise a chromogenic substrate for the enzyme.

The kit of the present invention preferably contains detailed instructions on the collection of the biological fluid, e.g., blood, the assay method and the interpretation of results. The types of assays which can be incorporated in kit form are many, and include, for example, including RIA, EIA, and ELISA.

In another embodiment of the present invention, the above-described antibodies are detectably labeled. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art.

Preferably, the paratopic molecules are detectably labeled through the use of radioisotopes, affinity labels, enzymatic labels, or fluorescent labels. Most preferably, the paratopic molecules are detectably labeled through the use of fluorochromes e.g., fluorescein isocyanate (FIC), fluorescein isothiocyanate (FITC), 5-dimethylamine-1-naphthalenesulfonyl chloride (DANSC), tetramethylrhodarnine isothiocyanate (TRITC), lissamine, rhodamine 8200 or sulphonyl chloride (RB 200 SC).

Example 1.

To detect IL-4 in vivo, BALB/c mice are injected with 10 μg of biotin- 1D11.2 or with saline, and, one hour later, with 1 μg of recombinant mouse IL-4. One day later, mice are bled and sera titered for IL-4, as described in Section 1.2., above, with the exception that an additional step is added to the ELISA (incubation of wells with serum was followed, after washing, by incubation with biotin-1D11.2, to identify IL-4 in the sera of mice that had not been injected with biotin-1D11.2). In addition, serial dilutions of recombinant IL-4 are added to the assay as a standard. No IL-4 (<7 pg/ml) is detectable in the serum of mice that have received only IL-4 one day before they were bled, while the serum of mice that receive both IL-4 and biotin-1D11.2 contains 37.2 ng of IL-4 per ml. This demonstrates that the injection ofbiotinyl-1D11.2 prevents the loss of injected IL-4 and allows it to be recovered from and detected in serum. BALB/c mice (3/group) are injected i. v. with saline or with 800 μg of goat antimouse IgD, which induces an IL-4 response that peaks 4–6 days later. Mice are injected five days later i.v. with 1% BALB/c serum, 10 μg of biotin-1D11.2, or 10 μg of biotin-TRFK4 (anti-IL-4 MAb) and are bled 5 hours after injection. Sera are assayed for IL-4 as described immediately above. Sera from mice that do not receive biotin-1D11.2 contains <7 pg/mi of IL-4 (the limit of detection in our assay system), while sera from mice that receive biotin-1D11.2, but not goat anti-mouse IgD contains 24.6±1.2 pg/ml of IL-4 and sera from mice that receive both goat anti-mouse IgD and biotin-1D11.2 contains 2,540±356 pg/ml of IL-4. This demonstrates that the present technique can specifically detect secreted IL4 by causing it to accumulate in serum. An additional group of mice in the same experiment is treated by injecting each mouse i v. with 800 μg of goat anti-mouse IgD antibody, then subcutaneously injected, 5 days later, with 10 μg ofbiotin-1D11.2. Mice are bled 5 hours after the second injection. ELISA of their sera reveal an IL-4 level of 1,260±869 pg/ml; thus, the present technique can be used with the modification that the labeled capture antibody is injected subcutaneously instead of intravenously.

What is claimed is:

1. A method of measuring the production of a secreted target analyte of interest in a human or animal, comprising the steps of:

a. injecting the human or animal with an amount of labeled neutralizing targeting moiety, wherein the targeting moiety binds specifically to the target analyte, and wherein the targeting moiety is injected in sufficient quantity that a measurable fraction of target analyte is bound by the labeled neutralizing targeting moiety;

b. allowing the targeting moiety to circulate through the injected human or animal for a defined period of time sufficient to bind to the target analyte of interest and form a targeting moiety:target analyte conjugate wherein the formation of the targeting moiety:target analyte conjugate decreases the clearing rate of the target analyte;

c. obtaining a sample of blood from the human or animal after the defined period of time;

d. combining the sample of blood with a capture moiety wherein the capture moiety binds specifically to the targeting moiety:target analyte conjugate in order to form an assay mixture;

e. incubating the assay mixture of step d to allow the capture moiety to bind to the targeting moiety:target analyte conjugate and form targeting moiety:target analyte:capture moiety complexes in the assay mixture;

f. removing any unbound and unconjugated targeting moiety and target analyte from the assay mixture;

g. detecting the amount of labeled targeting moiety:target analyte:capture moiety complexes;

wherein the amount of labeled targeting moiety:target analyte:capture moiety complexes detected provides a measure of the production of secreted target analyte in the sample during the defined period of time; and wherein the secreted target analyte is a secreted cytokine, secreted peptide or secreted protein hormone.

2. The method of claim 1, wherein the defined period of time is from about 1 hour to about 72 hours.

3. The method of claim 2, wherein the target analyte is a cytokine.

4. The method of claim 3, wherein the cytokine is selected from the group consisting of interleukins, interferons chemokines, growth factors, colony stimulating factors, lymphokines, lymphotoxins, and tumor necrosis factors.

5. The method of claim 3, wherein the cytokine is selected from the group consisting of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interferon-alpha, interferon-beta, interferon-gamma, lymphotoxin, tumor necrosis factor-alpha, transforming growth factor (TGF)-beta, granulocyte macrophage-colony stimulating factor (GM-CSF), nerve growth factor (NGF), and epidermal growth factor (EGF).

6. The method of claim 1, wherein the blood is selected from the group consisting of whole blood, serum and plasma.

7. The method of claim 1, wherein the targeting moiety is selected from the group consisting of antibodies, soluble receptors, and recombinant molecules with binding sites for the target analyte.

8. The method of claim 7, wherein the targeting moiety is a monoclonal antibody.

9. The method of claim 8, wherein the targeting moiety is detectably labeled, wherein the label is selected from the group consisting of radioisotopes, affinity labels, enzymatic labels, and fluorescent labels.

10. The method of claim 9, wherein the targeting moiety is labeled by linking to a fluorescent labeling compound.

11. The method of claim 10, wherein the fluorescent labeling compound is selected from the group consisting of fluorescein isothiocyanate, rhodamine, phycoerythrin, phycocyanin, allophycocyanin, o-phthaldehyde and fluorescamine.

12. The method of claim 9, wherein the labeled targeting moiety comprises first and second members of a complimentary ligand/anti-ligand pair, wherein the first member of the complimentary ligand/anti-ligand pair is injected as the targeting moiety in step (a); wherein the second member of the complimentary ligand/anti-ligand pair is a detectable binding partner to the first member; and wherein the method fuirther comprises the steps of (I) contacting the assay mixture after step (e) and before step (f) with the second member of the complimentary ligand/anti-ligand pair to allow binding of the first and second members; (II) removing any unbound second member; (III) detecting the amount of bound second member; and (IV) correlating the detected amount to the amount of targeting moiety:target analyte::capture moiety complexes in the assay mixture; wherein the amount of targeting moiety:target analyte:capture moiety complexes detected provides a measure of the production of secreted target analyte during the defined period of time.

13. The method of claim 12, wherein the first member of the complimentary ligand/anti-ligand pair is a monoclonal antibody.

14. The method of claim 13, wherein the capture moiety is an antibody.

15. The method of claim 14, wherein the capture moiety is a polyclonal antibody.

16. The method of claim 12, wherein the targeting moiety:target analyte:capture moiety complexes are detected by radioimmunoassay.

17. The method of claim 12, wherein the second member of the complimentary ligand/anti-ligand pair is detectably labeled by an enzymatic label.

18. The method of claim 17, wherein the label is a small molecule hapten.

19. The method of claim 18, wherein the hapten is biotin.

20. The method of claim 17, wherein the second member of the complimentary ligand/anti-ligand pair is selected from the group consisting of streptavidin, anti-biotin antibody, anti-hapten antibody, and anti-immunoglobulin antibody.

21. The method of claim 17, wherein the enzyme is selected from the group consisting of alkaline phosphatase, glucose oxidase, beta-galactosidase, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, asparaginase, ribonuclease, urease, catalase, glucose-6-phosphate dehydrogenase, glucoamylase and acetylcholinesterase.

22. The method of claim 12, wherein the second member of the complimentary ligand/anti-ligand pair is labeled with a fluorescent label.

23. The method of claim 22, wherein the fluorescent labeling compound is selected from the group consisting of fluorescein isothiocyanate, rhodamine, phycoerythrin, phycocyanin, allophycocyanin, o-phthaldehyde and fluorescamine.

24. The method of claim 1, wherein the capture moiety is an antibody.

25. The method of claim 24, wherein the antibody is a polyclonal antibody which recognizes many epitopes on the target analyte.

26. The method of claim 1, wherein the targeting moiety is labeled with a small molecule hapten and wherein the method fuirther comprises the step of binding the small molecule hapten to a binding partner which is conjugated to an enzyme.

27. The method of claim 26, wherein the hapten is biotin.

28. The method of claim 26, wherein the enzyme-conjugated binding partner is selected from the group consisting of streptavidin, anti-biotin antibody, anti-hapten antibody, and anti-immunoglobulin antibody.

29. The method of claim 26, wherein the enzyme is selected from the group consisting of alkaline phosphatase, glucose oxidase, beta-galactosidase, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, asparaginase, ribonuclease, urease, catalase, glucose-6-phosphate dehydrogenase, glucoamylase and acetylcholinesterase.

30. The method of claim 1 or 12, wherein the capture moiety is immobilized on a solid phase support.

* * * * *

UNITED STATES PATENT AND TRADEMARK OFFICE
CERTIFICATE OF CORRECTION

PATENT NO.    : 6,824,986 B1
DATED         : November 30, 2004
INVENTOR(S)   : Fred D. Finkelman and Suzanne C. Morris It is certified that error appears in the above-identified patent and that said Letters Patent is hereby corrected as shown below:

Title page,
Item [57], ABSTRACT,
Line 7, should read -- a person or experimental animal --.
Line 25, should read --animal. --

Column 5,
Line 18, should read -- a family of proteins called immunoglobulins that can --.
Line 26, should read -- antigen. Using the nomenclature of Jerne, --.
Line 66, should read -- in their various grammatical forms. --

Column 6,
Line 2, should read -- in their various grammatical forms. --
Line 66, should read -- is defined as growth, --.

Column 7,
Line 7, should read -- interleukin-4, interleukin-6, interferon-alpha --.

Column 8,
Line 30, should read -- hormones, --.

Column 9,
Line 11, should read -- pair is biotin/avidin --.

Column 10,
Line 13, should read -- Binding of the analyte/labeled --.
Line 47, should read -- "radioimmunoassay, an assay"

Column 12,
Line 32, should read -- cytokine-specific antiobiodies --.

Column 14,

UNITED STATES PATENT AND TRADEMARK OFFICE
CERTIFICATE OF CORRECTION

PATENT NO. : 6,824,986 B1
DATED : November 30, 2004
INVENTOR(S) : Fred D. Finkelman and Suzanne C. Morris It is certified that error appears in the above-identified patent and that said Letters Patent is hereby corrected as shown below:

Title page,
Item [57], ABSTRACT,
Line 7, should read -- a person or experimental animal --.
Line 25, should read --animal. --

Column 5,
Line 18, should read -- a family of proteins called immunoglobulins that can --.
Line 26, should read -- antigen. Using the nomenclature of Jerne, --.
Line 66, should read -- in their various grammatical forms. --

Column 6,
Line 2, should read -- in their various grammatical forms. --
Line 66, should read -- is defined as growth, --.

Column 7,
Line 7, should read -- interleukin-4, interleukin-6, interferon-alpha --.

Column 8,
Line 30, should read -- hormones, --.

Column 9,
Line 11, should read -- pair is biotin/avidin --.

Column 10,
Line 13, should read -- Binding of the analyte/labeled --.
Line 47, should read -- "radioimmunoassay, an assay"

Column 12,
Line 32, should read -- cytokine-specific antiobiodies --.

Column 14,
Line 37, should read -- container, or reagents capable of amplifying --.

UNITED STATES PATENT AND TRADEMARK OFFICE
CERTIFICATE OF CORRECTION

PATENT NO. : 6,824,986 B1
DATED : November 30, 2004
INVENTOR(S) : Fred D. Finkelman and Suzanne C. Morris It is certified that error appears in the above-identified patent and that said Letters Patent is hereby corrected as shown below:

Column 15,
Line 38, should read -- bilized on a solid phase support. A further --.
Line 57, should read -- interferon-alpha --.

Column 19,
Line 3, should read -- method further comprises --.

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,824,986 B1
APPLICATION NO. : 09/167088
DATED : November 30, 2004
INVENTOR(S) : Fred D. Finkelman and Suzanne C. Morris It is certified that error appears in the above-identified patent and that said Letters Patent is hereby corrected as shown below:

Column 5, Line 66, should be deleted on the Certificate of Correction.

Column 10, Line 47, should read -- radioimmunoassay, an assay --.

Column 10, Line 62, should read -- of labeled analyte binding --.

Signed and Sealed this

Fifth Day of September, 2006

JON W. DUDAS
*Director of the United States Patent and Trademark Office*